US00PP24685P2

(12) United States Plant Patent
Willemsen

(10) Patent No.: US PP24,685 P2
(45) Date of Patent: Jul. 22, 2014

(54) ***BRUNNERA* PLANT NAMED 'SILVER HEART'**

(50) Latin Name: *Brunnera macrophylla*
Varietal Denomination: Silver Heart

(71) Applicant: Peter Jan Willemsen, Veenendaal (NL)

(72) Inventor: Peter Jan Willemsen, Veenendaal (NL)

( * ) Notice: Subject to any disclaimer, the term of this patent is extended or adjusted under 35 U.S.C. 154(b) by 88 days.

(21) Appl. No.: 13/694,259

(22) Filed: Nov. 13, 2012

(51) Int. Cl.
*A01H 5/00* (2006.01)

(52) U.S. Cl.
USPC ..... Plt./412

(58) Field of Classification Search
USPC ..... Plt./412
See application file for complete search history.

*Primary Examiner* — Annette Para
(74) *Attorney, Agent, or Firm* — Penny J. Aguirre

(57) ABSTRACT

A new cultivar of *Brunnera macrophylla*, 'Silver Heart', characterized by its leaves that are large, strong, round-cordate in shape, and heavily mottled with silver with very thin green veins and margins, and its resistance to sun scorch.

2 Drawing Sheets

Botanical classification: *Brunnera macrophylla.*
Cultivar designation: 'Silver Heart'.

CROSS REFERENCE TO A RELATED APPLICATION

This application is co-pending with a U.S. Plant Patent Application filed for a plant derived from the same parentage that is entitled *Brunnera* Plant Named 'Sea Heart' (U.S. Plant patent application Ser. No. 13/694,253).

BACKGROUND OF THE INVENTION

The present invention relates to a new and distinct cultivar of *Brunnera macrophylla*, and is hereinafter referred to by the cultivar name 'Silver Heart'. 'Silver Heart' represents a new herbaceous perennial grown for use as a landscape plant.

The inventor discovered the new cultivar, 'Silver Heart', in August of 2010 as a naturally occurring chimeral mutation of *Brunnera macrophylla* 'Silver Lace' (not patented) that was growing in a container in a production block of 'Silver Lace' in Veenendaal, The Netherlands.

Asexual propagation of the new cultivar was first accomplished under the direction of the Inventor by tissue culture in January of 2011 in Heerhugowaard, The Netherlands. Propagation by tissue culture has determined the characteristics to be stable and reproduced true to type in successive generations.

SUMMARY OF THE INVENTION

The following traits have been repeatedly observed and represent the characteristics of the new cultivar. These attributes in combination distinguish 'Silver Heart' as a new and unique cultivar of *Brunnera.*

1. 'Silver Heart' exhibits large, strong leaves.
2. 'Silver Heart' exhibits mature leaves that are heavily mottled with silver with very thin green veins and margins.
3. 'Silver Heart' exhibits mature leaves that are round-cordate in shape.
4. 'Silver Heart' exhibits resistance to sun scorch.

'Silver Lace', the parent plant of 'Silver Heart', differs from 'Silver Heart' in having leaves that are thinner, weaker, prone to sun scorch, and exhibit much less silver coloration. 'Silver Heart' can be most closely compared to the cultivars 'Looking Glass' (U.S. Plant Pat. No. 17,829), 'Jack Frost' (U.S. Plant Pat. No. 13,859), 'Silver Wings' (U.S. Plant Pat. No. 13,706), 'Emerald Mist' (U.S. Plant Pat. No. 20,460) and 'Sea Heart'. 'Looking Glass' differs from 'Silver Heart' in having thinner and weaker leaves, and in being prone to sun scorch. 'Jack Frost' differs from 'Silver Heart' in having leaves that are thinner, weaker, less rounded in shape, and prone to sun scorch. 'Silver Wings' differs from 'Silver Heart' in leaves that are less rounded with much less distinct silver mottling with a thin white margin. 'Emerald Mist' differs from 'Silver Heart' in having leaves with silver mottling on the outer portion of the leaf blade with leaf centers green in color. 'Sea Heart' is similar to 'Silver Heart' in having round-cordate strong leaves that are sun tolerant, however 'Sea Heart' differs from 'Silver Heart' in having leaves with less silver mottling.

BRIEF DESCRIPTION OF THE DRAWING

The accompanying colored photographs illustrate the overall appearance and distinct characteristics of the new *Brunnera*. The photographs were taken of a plant about one year in age as field grown outdoors and placed in a two-gallon container for the photographs.

The photograph in FIG. 1 provides a side view of 'Silver Heart' in bloom.

Figure 1:
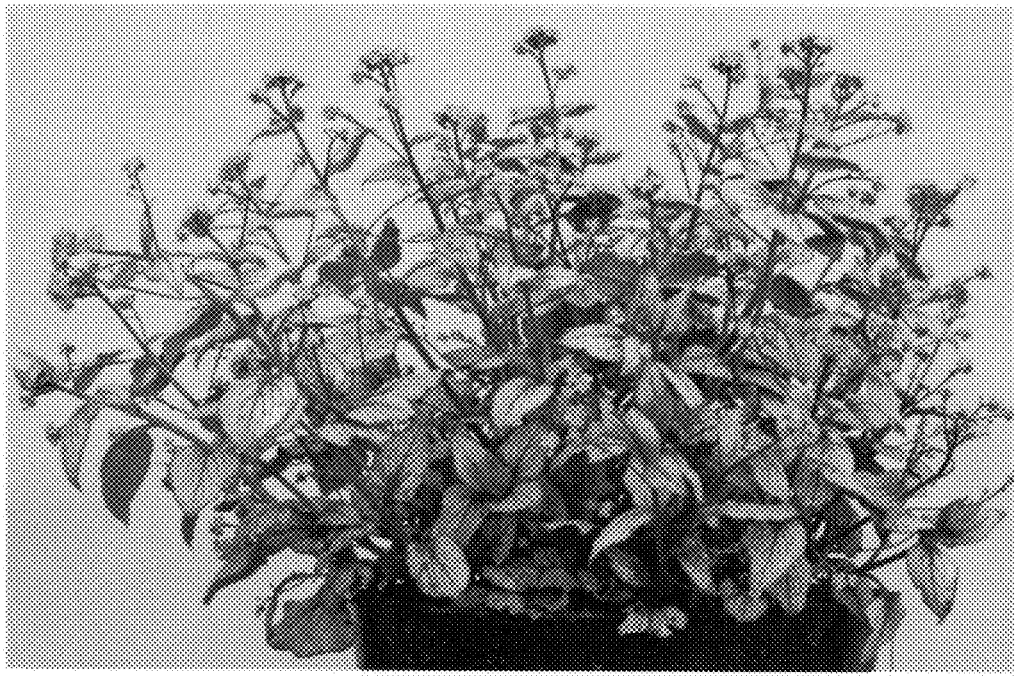
Figure 2:
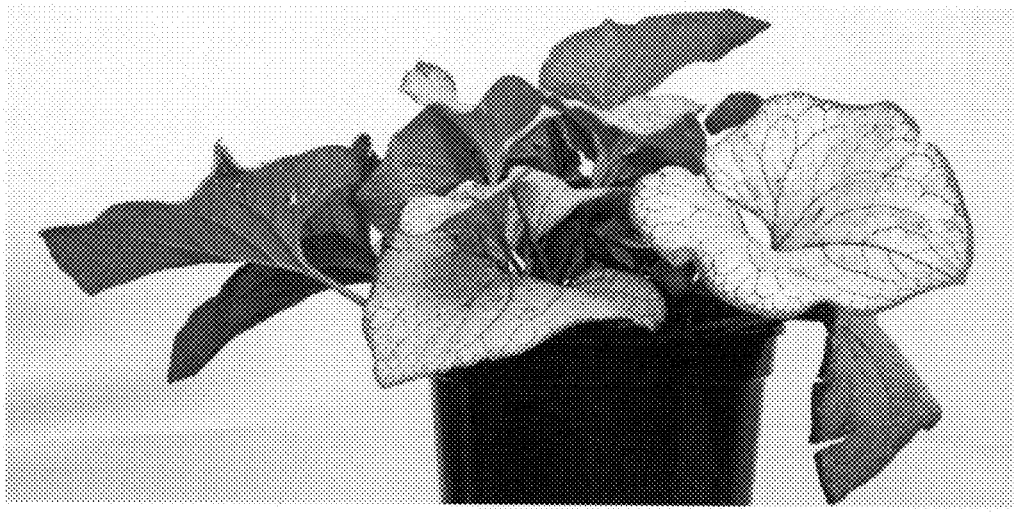

The photograph in FIG. 2 provides a side view of 'Silver Heart' in late summer.

Figure 3:
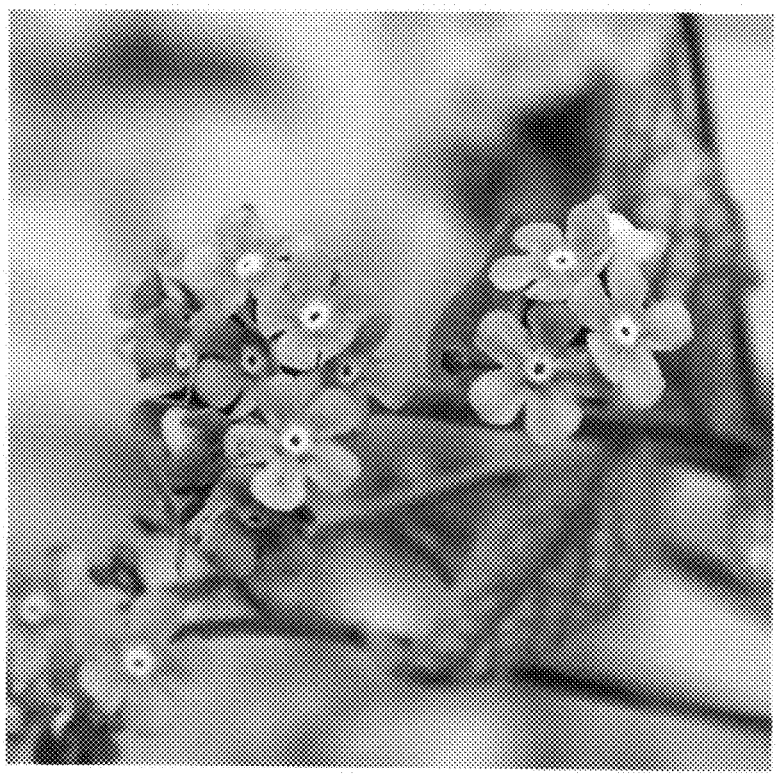

The photograph in FIG. 3 provides a close-up view of the flowers of 'Silver Heart'.

Figure 4:
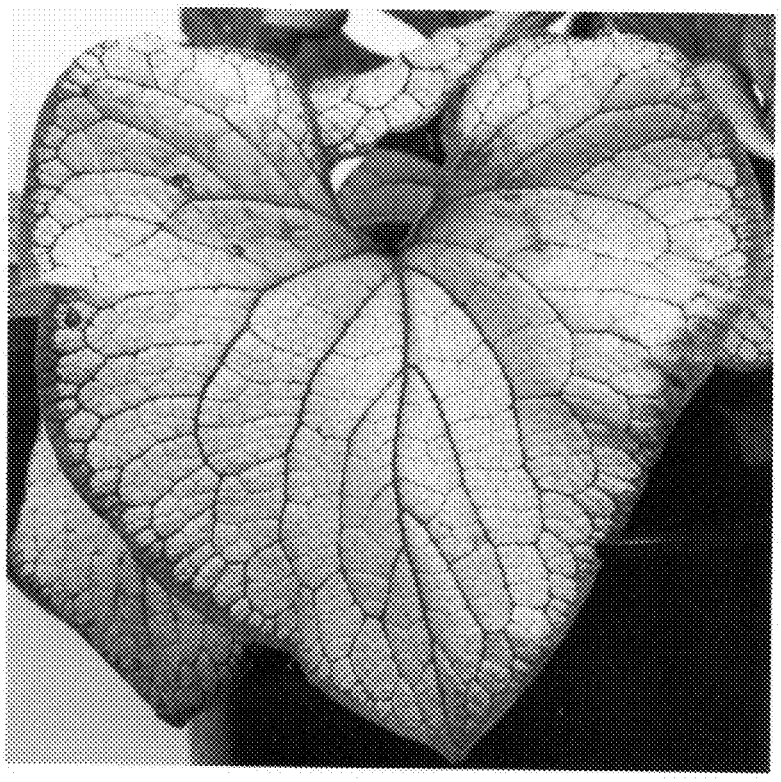

The photograph in FIG. 4 provides a close-up view of a mature leaf of 'Silver Heart'. The colors in the photographs may differ slightly from the color values cited in the detailed botanical description, which accurately describe the colors of the new *Brunnera.*

DETAILED BOTANICAL DESCRIPTION OF THE PLANT

The following is a detailed description of one year-old plants of the new cultivar as field grown in Zuidwolde, The Netherlands. Plants were grown under average day temperatures ranging from 14° to 28° C. (August) to 8° to 16° C. (April) and average night temperatures of 6° to 16° C. (August) to 3° to 10° C. (April). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—April in The Netherlands.

*Plant type*.—Herbaceous perennial.

*Plant habit*.—Clump-forming, open mound with flowering stems emerging from basal rosette of foliage.

*Height and spread*.—Average of 32.7 cm in height and 61.2 cm in width.

*Hardiness*.—At least hardy in U.S.D.A. Zones 3 to 9.

*Diseases and pests*.—No more susceptible or resistant to pests and diseases than other *Brunnera* varieties.

*Root description*.—Fibrous, medium in thickness and sparse in density.

*Branching habit*.—No lateral branches, leaves grow in basal rosettes, flowering stems arise from the centers of the rosettes before the mature leaves are formed.

*Propagation*.—Tissue culture.

*Growth rate*.—Moderately vigorous.

Stem description (flowering stem):

*Shape*.—Round.

*Stem color*.—146C to 146D, tinged with 148A.

*Stem size*.—An average of 26.1 cm in length and 0.5 mm in diameter.

*Stem surface*.—Moderately glossy, angulate, densely covered with short scabrous hairs, 0.7 mm in length and 157C to 157D in color.

*Stem aspect*.—Average angle of 50° to soil.

*Stem strength*.—Strong.

*Stem number*.—An average of 46 main flowering stems.

*Internode*.—Average length is 2.9 cm.

Foliage description:

*Leaf shape*.—Round-cordate.

*Leaf division*.—Single.

*Leaf base*.—Oblique, lobes at the base free to slightly overlapping.

*Leaf apex*.—Broad acute.

*Leaf venation*.—Pinnate-laciniate, color: upper surface; N137A, lower surface; 148B.

*Leaf margins*.—Entire.

*Leaf attachment*.—Petiolate.

*Leaf arrangement*.—Alternate on cauline leaves and basal leaves are in rosettes.

*Leaf surface*.—Upper surface is slightly glossy and rugose, lower surface is dull, rugose, both surfaces are rough to the touch due to being heavily pubescent; short scabrous hairs are an average of 0.7 mm in length and between 157C and 157D in color.

*Leaf substance*.—Strong.

*Leaf variegation pattern*.—Heavily mottled with Silver on entire upper leaf surface with thin green veins and margins.

*Leaf color*.—Young upper surface; 138B veined 143A, young lower surface; 143A to 143B, mature upper surface; 194B with a silvery shine, margins and veins N137A, mature lower surface; 137C.

*Leaf size*.—Average of 20.4 cm in length and 18.5 cm in width.

*Leaf quantity*.—Average of 7 per rosette.

*Cauline leaves*.—Average of 5, ovate in shape, sessile, average of 7 cm in length and 6 cm in width, acute apex, cuneate base, color, venation and surface match basal leaves.

*Petioles*.—Average of 17.3 cm in length and 4.5 mm in width, 144A in color, base strongly tinged with N199A.

Flower description:

*Inflorescence type*.—Axillary and terminal paniculate cymes of rotate flowers on leafy flowering stems that arise from base with smaller panicles from upper nodes.

*Inflorescence size*.—Average of 5 cm in height and about 1.7 cm in width.

*Flower fragrance*.—Faint, sweet and somewhat unpleasant.

*Flower quantity*.—Average of 150 per lateral stem, average of 15 per inflorescence.

*Flower lastingness*.—Average of one week, self-cleaning.

*Flower buds*.—Broad obovate and top flattened in shape, average of 2.5 mm in diameter and 2 mm in depth, approximately 30% of the flower buds open at one stage, 85C with green base 143B to 143C in color.

*Flower aspect*.—Held upright to slightly outward.

*Flower size*.—Average of 7 mm in diameter and 2.5 mm in depth.

*Petals*.—Rotate, average of 5, broadly obovate in shape, lower 20% fused at base, margin is entire, about 3.5 mm in length and 2.5 mm in width, apex is rounded, upper and lower surfaces are dull and moderately velvety, color: when opening upper side; 96C, base 85A turning to N155A, when opening lower side; 92B, when fully opened upper side; 100B, base N155A, when fully opened lower side; 97A, petal color fading to 101B.

*Calyx*.—Campanulate, about 1.5 mm in width and 2 mm in length.

*Sepals*.—5, Rotate and campanulate, ovate in shape, about 2 mm in length and 0.75 mm in width, margin is entire, apex is acute, cuneate base lower 25% fused, upper surface smooth and slightly glossy, lower side dull and moderately pubescent and covered with small pubescent hairs 0.2 mm in length and 157D in color, color: immature upper surface; 143A to 143B, immature lower surface; 143B to 143C, mature upper surface; 143A, mature lower surface; 143B.

*Peduncles*.—Average of 4.5 cm in length and 1 mm in diameter, an average angle of 50° to main stem, moderately strong, and 147A in color.

*Pedicels*.—Average of 5 mm, in length and about 0.5 mm in diameter, an average angle of 45° to main stem, moderately strong, and 147A in color.

Reproductive organs:

*Gynoecium*.—1 Pistil, about 1 mm in length, stigma is club-shaped and 145C in color, ovary is 0.8 mm in length and 145C in color, ovary is 144A to 144B in color.

*Androcoecium.*—5 stamens, anther is dorsifixed, kidney shaped, about 0.5 mm in length and 203A in color, filament 0.5 mm in length and NN155D in color, pollen is low in quantity and 155D in color.

*Seed*.—No fruits or seed detected to date.

It is claimed:

1. A new and distinct cultivar of *Brunnera* plant named 'Silver Heart' as herein illustrated and described.

* * * * *